United States Patent [19]
Ohnishi

[11] Patent Number: 5,053,556
[45] Date of Patent: Oct. 1, 1991

[54] PROCESS FOR PRODUCING ALKENYL ETHERS

[75] Inventor: Noriyuki Ohnishi, Minamatashi, Japan

[73] Assignee: Chisso Corporation, Osaka, Japan

[21] Appl. No.: 466,582

[22] Filed: Jan. 17, 1990

[30] Foreign Application Priority Data

Jan. 31, 1989 [JP] Japan .................................. 1-21778
Apr. 10, 1989 [JP] Japan .................................. 1-90356
Apr. 25, 1989 [JP] Japan .................................. 1-105081
May 25, 1989 [JP] Japan .................................. 1-132407
May 26, 1989 [JP] Japan .................................. 1-133883

[51] Int. Cl.$^5$ .............................................. C07L 41/01
[52] U.S. Cl. ..................................... 568/675; 568/673; 568/687; 568/579; 568/654; 568/618; 568/619
[58] Field of Search ............... 568/687, 673, 675, 574, 568/654, 618, 619

[56] References Cited

U.S. PATENT DOCUMENTS 2,962,534 11/1960 Montagna et al. .................. 568/687
3,359,324 12/1987 Hirsh .................................... 568/687
4,307,252 12/1981 Weber ................................... 568/450

Primary Examiner—Howard T. Mars
Attorney, Agent, or Firm—Fred Philpitt

[57] ABSTRACT

A one-step process for producing an alkenyl ether in only one step and under mild conditions by reacting an aldehyde of the formula $$R^1-\underset{\underset{R^4}{|}}{\overset{\overset{R^2}{|}}{C}}-CHO$$

with an alcohol of the formula $$R^3-OH$$

in the presence of an acidic catalyst in liquid phase, and recovering as the reaction product an alkenyl ether of the formula $$R^5-\underset{\underset{R^2}{|}}{C}=CH-OR^3$$

wherein
 $R^1$ is a 2-8 C alkyl or $R-CH_2-CH=$ wherein R is a 1-8 C alkyl group,
 $R^2$ is a 1-6 C alkyl,
 $R^3$ is a linear or branched 6-12 C alkyl, a cyclohexyl, a hydroxyhexamethylenyl or $$-(CH_2-\underset{\underset{R'}{|}}{CH}-O)_nH$$

wherein R' is H and n is 2 or 3,
 $R^4$ is hydrogen or $R-CH_2-CH=$ wherein R is a 1-8 C alkyl group, and
 $R^5$ is a 2-8 C alkyl or $R-CH=CH-$ wherein R is a 1-8 C alkyl.

9 Claims, No Drawings

PROCESS FOR PRODUCING ALKENYL ETHERS

BACKGROUND OF THE INVENTION

1. Field of the Invention

This invention relates to a process for producing alkenyl ethers. More particularly it relates to a process for producing an α,β-unsaturated ether, an unsaturated ether having conjugated double bonds, a hydroxyalkenyl ether or a hydroxyalkenyl ether having conjugated double bonds.

2. Description of the Related Art

As to conventional processes for producing α,β-unsaturated ethers, for example the following synthesis is disclosed in J. Org. Chem., 23, 670 (1958):

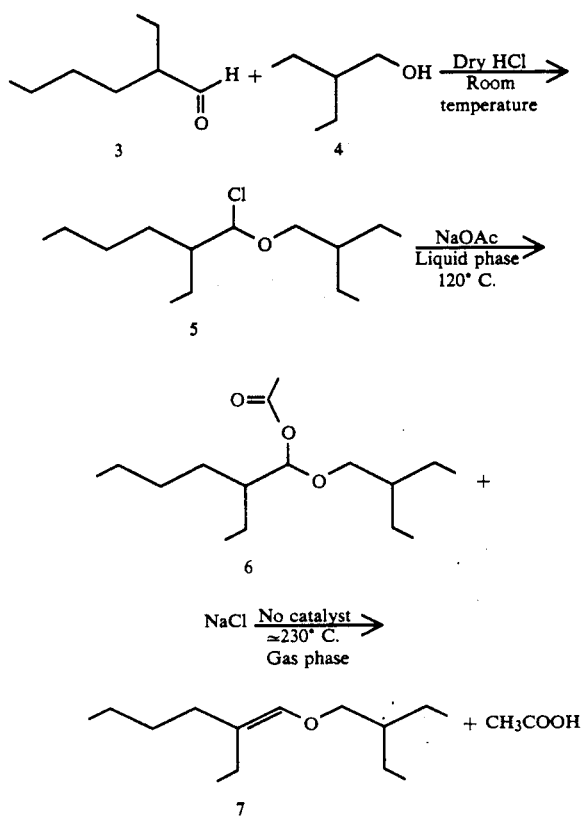

Namely, from 2-ethylhexylaldehyde of the formula 3 and 2-ethylbutyl alcohol of the formula 4 is prepared 1-chloro-2-ethylhexyl-2'-ethylbutyl ether of the formula 5, which is converted into 1-acetoxy-2-ethylhexyl-2'-ethylbutyl ether of the formula 6, from which acetic acid is removed in gas phase at 230° C., to prepare 2-ethylhexenyl-2-ethylbutyl ether of the formula 7. In general, most of production processes of α,β-unsaturated ethers have been carried out by subjecting acetals to catalytically thermal decomposition in gas phase at a high temperature of 300° to 800° C., as disclosed in Japanese patent application laid-open No. Sho 57-185232/1982, etc.

However, such conventional production processes of α,β-unsaturated ethers have drawbacks of requiring two or three steps starting from aldehydes and also requiring high temperatures in gas phase reaction.

Further, as to the production process of an unsaturated α,β-ether having conjugated double bonds, the following synthesis is disclosed in J. Polym. Sci., Part A-1, Vol. 9, 164, 1971:

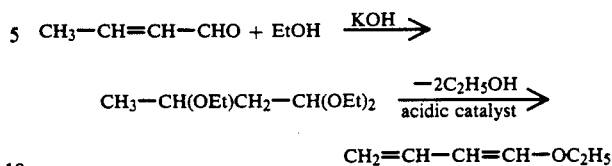

Namely, from an unsaturated aldehyde and an alcohol is prepared a 3-alkoxyacetal in the presence of an alkali catalyst, followed by removing the alcohol from the acetal in liquid phase in the presence of an acidic catalyst to prepare an unsaturated ether having conjugated double bonds.

However, this synthesis also requires two stages.

Thus, a commercial production process wherein the number of steps starting from aldehydes is small and the reaction is carried out under mild conditions has been desired.

Next, the prior art of production process of hydroxyalkenyl ethers among unsaturated ethers having conjugated double bonds will be described.

A synthesis of a vinyl ether among hydroxyalkenyl ethers is disclosed in U.S. Pat. No. 3,429,845 or Ann. Chem., 601, 81 (1956). In this synthesis, an alkane diol is added to acetylene. However, according to such a process, high temperature and high pressure are required for the reaction, and byproducts such as a divinyl compound (CH=CHOAOCH=CH) or a cyclic acetal are formed in a large quantity; hence the process is unsuitable as a commercial means.

On the other hand, a process of reacting ethanediol with an alkyl vinyl ether in the presence of mercuric acetate is disclosed in J. Am. Chem. Soc., 79, 2828 (1957). According to this process, main products are dioxolan and divinyl ether and 2-hydroxyethyl vinyl ether forms as a byproduct; hence it is impossible to employ this process as a production process of hydroxyalkenyl ethers.

Since such a hydroxyalkenyl ether having conjugated double bonds has conjugated double bonds, the ether can be expected as a functional monomer. Such a hydroxyalkenyl ether having conjugated double bonds is a novel substance.

As apparent from the foregoing, the object of the present invention is to provide a process for producing alkenyl ethers from an aldehyde at one step and under mild reaction conditions.

SUMMARY OF THE INVENTION

The present invention has the following main constitution 1) and constitutions as embodiments 2)–5):

1) A process for producing an alkenyl ether, which comprises reacting an aldehyde expressed by the formula (1)

with an alcohol of the formula (2)

in the presence of an acidic catalyst in liquid phase, to produce an alkenyl ether expressed by the formula (3)

$$R^5-\underset{R^2}{C}=CH-OR^3 \qquad (3)$$

wherein $R^1$ represents an alkyl group of 2 to 8 carbon atoms, $R^4$ represents hydrogen atom or $R^1$ and $R^4$ each represent $R-CH_2-CH=$ group wherein R represents an alkyl group of 1 to 8 carbon atoms; $R^2$ represents an alkyl group of 1 to 6 carbon atoms; $R^3$ represents a linear or branched alkyl group of 4 to 24 carbon atoms, a cycloalkyl group of 4 to 15 carbon atoms, preferably 4 to 7 carbon atoms, a linear or branched oxyalkyl group of 5 to 10 carbon atoms, an oxycycloalkyl group of 4 to 15 carbon atoms, preferably 4 &o 7 carbon atoms or $$-(CH_2-\underset{R'}{CH}-O)_nH \text{ group}$$

wherein R' represents hydrogen atom or methyl group and n represents an integer of 2 to 20; and $R^5$ represents an alkyl group of 2 to 8 carbon atoms or $R-CH=CH-$ group wherein R is as defined above.

2) A process for producing an alkenyl ether according to item 1), which comprises reacting an aldehyde expressed by the formula $$\underset{R^1-CH-CHO}{\overset{R^2}{|}} \qquad (1-1)$$

with an alcohol expressed by the formula $$R^{3'}-OH \qquad (2-1)$$

in a molar ratio of 0.1:1 to 10:1, in the presence of an acidic catalyst in liquid phase, to produce an α,β-unsaturated ether expressed by the formula $$\underset{R^1-C=CH-OR^{3'}}{\overset{R^2}{|}} \qquad (3-1)$$

wherein $R^1$ represents an alkyl group of 2 to 8 carbon atoms, $R^2$ represents an alkyl group of 1 to 6 carbon atoms and $R^{3'}$ represents a linear or branched alkyl group of 4 to 24 carbon atoms or a cycloalkyl group of 4 to 15 carbon atoms, preferably 4 to 7 carbon atoms.

3) A process for producing an alkenyl ether according to item 1), which comprises reacting an aldehyde expressed by the formula $$R-CH_2-CH=\underset{R^2}{\overset{|}{C}}-CHO \qquad (1-2)$$

with an alcohol expressed by the formula $$R^{3'}-OH \qquad (2-1)$$

in the presence of an acidic catalyst in liquid phase, to produce an unsaturated ether having conjugated double bonds expressed by the formula $$R-CH=CH-\underset{R^2}{\overset{|}{C}}=CH-OR^{3'} \qquad (3-2)$$

wherein R represents an alkyl group of 1 to 6 carbon atoms, $R^2$ represents an alkyl group of 1 to 6 carbon atoms and $R^{3'}$ represents an alkyl group of 4 to 24 carbon atoms or a cycloalkyl group of 4 to 15 carbon atoms, preferably 4 to 7 carbon atoms 4) A process for producing an alkenyl ether according to item 1), which comprises reacting an aldehyde expressed by the formula $$\underset{R_2}{\overset{R_1-CH-CHO}{|}} \qquad (1-1)$$

with a diol expressed by the formula $$HOAOH \qquad (2-2)$$

or the formula $$\underset{R'}{\overset{HO(CH_2CHO)_nH}{|}} \qquad (2-3)$$

in a molar ratio of 0.05:1 to 10:1, in the presence of an acidic catalyst and in liquid phase, to produce a hydroxyalkenyl ether expressed by the formula $$\underset{R_2}{\overset{R_1-C=CH-OAOH}{|}} \qquad (3-3)$$

or $$\underset{R_2}{\overset{R_1-C=CH-O(CH_2CHO)_nH}{|}}\underset{R'}{\overset{|}{}} \qquad (3-4)$$

wherein $R_1$ represents an alkyl group of 2 to 8 carbon atoms, $R_2$ represents an alkyl group of 2 to 6 carbon atoms, R' represents hydrogen atom or methyl group, n represents an integer of 2 to 20 and A represents a linear, branched or cyclic alkylene group of 5 to 10 carbon atoms.

5) A process for producing an alkenyl ether according to item 1), which comprises reacting an aldehyde expressed by the formula $$R-CH_2-CH=\underset{R_2}{\overset{|}{C}}-CHO \qquad (1-2)$$

with a diol expressed by the formula $$HOAOH \qquad (2-2)$$

or $$\underset{R'}{\overset{HO(CH_2CHO)_nH}{|}} \qquad (2-3)$$

in a molar ratio of 0.05:1 to 10:1, in the presence of an acidic catalyst and in liquid phase, to produce a hydroxyalkenyl ether having conjugated double bonds, expressed by the formula

　(3-4)

or

　(3-5)

wherein R represents an alkyl group of 1 to 8 carbon atoms, $R_2$ represents an alkyl group of 1 to 6 carbon atoms, R' represents hydrogen atom or methyl group, n represents an integer of 2 to 20 and A represents a linear, branched or cyclic alkylene group of 5 to 10 carbon atoms.

DETAILED DESCRIPTION OF PREFERRED EMBODIMENTS

Examples of the aldehyde used in the present invention are higher aldehydes having a substituent at α-position thereof (see the above items 2) and 4)) such as 2-methylbutyraldehyde, 2-methylvaleraldehyde, 2-methylpentylaldehyde, 2-methylhexylaldehyde, 2-ethylbutylaldehyde, 2-ethylhexylaldehyde, etc., and higher alkenyl aldehydes having a substituent at α-position thereof (see the above items 3) and 5)) such as 2-ethylhexenal, 2-methylpentenal, 2-methylhexenal, etc.

Examples of the alcohol used in the present invention are higher alkanols of 4 to 24 carbon atoms (see $R^{3'}$-OH of the above items 2) and 3)) such as hexanol, 2-ethylbutanol, n-octanol, 2-ethylhexanol, pentanol, cyclohexanol, etc., diols (see HOAOH or

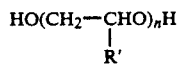

of the above items 4) and 5)) such as hexamethylene glycol, diethylene glycol, triethylene glycol, dipropylene glycol, tripropylene glycol, polyethylene glycol, polypropylene glycol, etc., phenols such as hydroquinone, resorcin, alkylsubstitutes thereof, etc. In the case where the above A has 4 carbon atoms or less (such as ethanediol, 1,4-butanediol, etc.) and in the case of catechol, cyclic acetals are formed as a main component.

Examples of the acidic catalyst used in the present invention are ferric chloride, titanous chloride, titanic chloride, aluminum chloride, zinc chloride, nickel chloride, cobalt chloride, calcium chloride, cation exchange resin, activated clay, molecular sieves, p-toluenesulfonic acid, sulfuric acid, hydrochloric acid, N-hydroxybenzenesulfonamide, etc.

The molar ratio of the aldehyde to the alcohol is 0.5:1 to 10:1, preferably 1:1 to 3:1 in the case of the above items 2) and 3), and the molar ratio of the aldehyde to the diol is 0.05:1 to 10:1, preferably 0.1:1 to 2:1 in the case of the above items 4) and 5).

The quantity of the catalyst used is in the range of 0.01 to 10% by weight, preferably 0.05 to 2% by weight based on the aldehyde. The quantity of N-hydroxybenzenesulfonamide is suitably in the range of 1 to 2%, and that of ferric chloride is suitably in the range of 0.05 to 0.1%, preferably 0.05 to 0.5%. Catalysts soluble in mineral oils are added in a quantity of 0.01 to 5% by weight, preferably 0.05 to 2% by weight. If the quantity is less than the above quantity, there is no catalytic activity, while if it exceeds the above quantity, aldehyde condensation occurs to cause aldehyde loss. Further, it is more preferred to again add the catalyst midway during the reaction.

The reaction temperature of the present invention varies depending on the aldehyde and alcohol used, but anyhow, when formed water is continuously withdrawn in a reflux state of the reaction solution of the aldehyde and the alcohol, the reaction proceeds and the aldehyde and alcohol used are almost insoluble in water so that it is not particularly necessary to use any azeotropic solvent for separating formed water, but it does not matter if the solvent is used. Further, as to the reaction pressure, any one of normal pressure, reduced pressure and elevated pressure may be employed, but usually, normal pressure reaction which is easy in operation may be sufficient.

The effectiveness of the present invention consists in that α,β-unsaturated ethers so far prepared from aldehydes by way of two or three steps could have this time been prepared at only one step, and further in that gas phase reaction at a high temperature of 300° to 800° C. has so far been carried out, but instead, reaction under a mild condition of 200° C. or lower could have this time become possible.

According to the production process of the present invention, it is possible to obtain an unsaturated ether having conjugated double bonds at only one step from an aldehyde.

Further, according to the production process of the present invention, it is possible to obtain a hydroxyalkenyl ether under mild reaction conditions and with a high selectivity by directly acetalizing an alkane diol, a glycol or a hydroquinone in the presence of an acidic catalyst, using an aldehyde having an alkyl substituent at its α-position as a raw material.

Further, according to the production process of the present invention, a hydroxyalkenyl ether having conjugated double bonds, which can be expected as a functional monomer, can be produced from easily commericially available unsaturated aldehyde and diol as raw materials, under a mild condition of a reflux temperature of the aldehyde of 200° C. or lower and with a high selectivity; hence the production process is a commercially excellent process.

According to the production process of the present invention, it is possible to produce alkenyl ethers with a good selectivity.

The present invention will be described in more detail by way of Examples and Comparative examples but it should not be construed to be limited thereto.

EXAMPLE 1

2-Ethylhexylaldehyde (64 parts by weight), hexanol (50 parts by weight) and N-hydroxybenzenesulfonamide (1.1 part by weight) were fed into a four-neck flask, followed by reacting them on heating under reflux with stirring for 4 hours while continuously withdrawing formed water. As a result, the conversion of hexanol was 93.1%, the selectivity of 2-ethylhexenyl hexyl ether was 97.4% and the remainder 2.6% was an acetal.

EXAMPLE 2.

2-Ethylbutyraldehyde (50 parts by weight), 2-ethylbutyl alcohol (50 parts by weight) and ferric chloride (0.1 part by weight) were subjected to the same procedure as in Example 1. As a result, the conversion of 2-ethylbutyl alcohol was 93.6%, the selectivity of 2-ethylbutenyl-2-ethylbutyl ether was 67.2% and the remainder 32.8% was an acetal.

EXAMPLE 3

2-Ethylhexylaldehyde (186 parts by weight), lauryl alcohol (185 part by weight) and p-toluenesulfonic acid (0.4 part by weight) were subjected to the same procedure as in Example 1. As a result, the conversion of lauryl alcohol was 97.8%, the selectivity of 2-ethylhexenyl lauryl ether was 100% and no acetal formation was observed.

EXAMPLE 4

2-Ethylhexylaldehyde (154 parts by weight), octanol (128 parts by weight) and aluminum chloride (0.3 part by weight) were subjected to the same procedure as in Example 1. As a result, the conversion of octanol was 88.3%, the selectivity of 2-ethylhexenyl octyl ether was 92.6% and the remainder 7.4% was an acetal.

EXAMPLE 5

2-Ethylhexylaldehyde (154 parts by weight), cyclohexanol (100 parts by weight) and p-toluenesulfonic acid (0.3 part by weight) were subjected to the same procedure as in Example 1. As a result, the conversion of cyclohexanol was 86.8%, the selectivity of 2-ethylhexenyl cyclohexyl ether was 100% and no acetal formation was observed.

COMPARATIVE EXAMPLE 1

When n-hexanal was used in place of 2-ethylbutyraldehyde in Example 2, 100% of an acetal formed and no alkenyl ether formation was observed.

COMPARATIVE EXAMPLE 2

When the same aldehyde and alcohol as in Example 1 and FeCl$_3$ as a catalyst were cooled with dry ice-acetone and reacted at about −30° C., an acetal formed predominantly.

EXAMPLE 6

2-Methylvaleraldehyde (120 parts by weight), hexanol (100 parts by weight) and p-toluenesulfonic acid (0.2 part by weight) were fed into a four-neck flask, followed by reacting them on heating under reflux with stirring for 4 hours, while continuously withdrawing formed water. As a result, the conversion of hexanol was 84.6%, the selectivity of 2-methylpentenyl hexyl ether was 87.3% and the remainder 12.7% was an acetal.

EXAMPLE 7

2-Methylhexylaldehyde (134 parts by weight), cyclohexanol (100 parts by weight) and zinc chloride (0.2 part by weight) were subjected to the same procedure as in Example 6. As a result, the conversion of cyclohexanol was 85.0%, the selectivity of 2-methylhexenyl cyclohexyl ether was 92.0% and the remainder 8.0% was an acetal.

EXAMPLE 8

2-Methylvaleraldehyde (120 parts by weight), lauryl alcohol (185 parts by weight) and aluminum chloride (0.3 part by weight) were subjected to the same procedure as in Example 6. As a result, the conversion of lauryl alcohol was 97.5%, the selectivity of 2-methylpentenyl lauryl ether was 100% and no acetal formation was observed.

COMPARATIVE EXAMPLE 3

When n-hexanal was used in place of 2-methylvaleraldehyde of Example 6, an acetal was formed in 100% and no alkenyl ether formation was observed.

COMPARATIVE EXAMPLE 4

Example 6 was repeated except that reaction was carried out under cooling with dry ice-acetone at about −30° C. As a result, an acetal formed predominantly.

EXAMPLE 9

2-Ethylhexenal (63 parts by weight), 2-ethylhexanol (64 parts by weight) and p-toluenesulfonic acid (0.1 part by weight) were fed into a four-neck flask, followed by reacting them on heating with stirring under reflux for 5 hours while continuously withdrawing formed water. As a result, the conversion of 2-ethylhexanol was 88.2%, and the selectivity of formation of 1-(2'-ethylhexoxy)-2- ethyl-1,3-hexadiene was 91%.

EXAMPLE 10

2-Methylpentenal (49 parts by weight), hexanol (50 parts by weight) and aluminum chloride (0.1 part by weight) were subjected to the same procedure as in Example 9. As a result, the conversion of hexanol was 91.0% and the selectivity of 1-hexoxy-2-methyl-1,3-pentadiene was 92.5%.

EXAMPLE 11

2-Methylhexenal (56 parts by weight), cyclohexanol (50 parts by weight) and N-hydroxybenzenesulfonamide (1 part by weight) were subjected to the same procedure as in Example 9. As a result, the conversion of cyclohexanol was 94.3% and the selectivity of formation of 1-cyclohexoxy-2-methyl-1,3-hexadiene was 95.6%.

EXAMPLE 12

2-Ethylhexanal (128 parts by weight), hexamethylene glycol (118 parts by weight) and p-toluenesulfonic acid (0.2 part by weight) were fed into a four-neck flask, followed by reacting them on heating with stirring under reflux for 2 hours while continuously withdrawing formed water. As a result, the conversion of hexamethylene glycol was 85% and the selectivity of formation of hexamethylene glycol mono-2-ethylhexenyl ether was 65%.

EXAMPLE 13

2-Ethylhexanal (128 parts by weight), triethylene glycol (150 part by weight) and ferric chloride (0.5 part by weight) were subjected to the same manner as in Example 12. As a result, the conversion of triethylene glycol was 88% and the selectivity of formation of triethylene glycol mono-2-ethylhexenyl ether was 73.5%.

EXAMPLE 14

2-Methylvaleraldehyde (100 parts by weight), dipropylene glycol (134 part by weight) (containing isomers) were subjected to the same manner as in Example 12. As a result, the conversion of dipropylene glycol was 81% and the selectivity of formation of dipropylene glycol mono-2-methylpentenyl ether was 76%.

COMPARATIVE EXAMPLE 5

Hexanal (100 parts by weight), dipropylene glycol (134 parts by weight) (containing isomers) and aluminum chloride (0.4 part by weight) were subjected to the same procedure as in Example 12. As a result, a cyclic acetal formed as a main component and formation of hydroxyalkenyl ether could not be observed.

EXAMPLE 15

2-Ethylhexenal (126 parts by weight), diethylene glycol (106 parts by weight) and ferric chloride (1.2 part by weight) were fed into a four-neck flask, followed by reacting them on heating with stirring under reflux for 5 hours while continuously withdrawing formed water. As a result, the conversion of diethylene glycol was 88% and the selectivity of formation of diethylene glycol mono-2-ethyl-1,3-hexadienyl ether was 77%.

EXAMPLE 16

2-Ethylhexenal (128 parts by weight), triethylene glycol (150 parts by weight) and aluminum chloride (1.2 part by weight) were subjected to the same procedure as in Example 15. As a result, the conversion of triethylene glycol was 86% and the selectivity of formation of triethylene glycol mono-2-ethyl-1,3-hexadienyl ether was 80%.

What I claim is:

1. A one-step process for producing an alkenyl ether, which comprises reacting an aldehyde having the formula $$R^1-\underset{\underset{R^4}{|}}{\overset{\overset{R^2}{|}}{C}}-CHO$$

with an alcohol of the formula $$R^3-OH$$

in the presence of an acidic catalyst in liquid phase, and recovering as the reaction product an alkenyl ether of the formula $$R^5-\underset{\underset{R^2}{|}}{C}=CH-OR^3$$

wherein
  $R^1$ is an alkyl group of 2-8 carbon atoms or a R—CH$_2$—CH= group wherein R represents an alkyl group of 1-8 carbon atoms,
  $R^2$ represents an alkyl group of 1-6 carbon atoms,
  $R^3$ represents a linear or branched alkyl group having 6-12 carbon atoms, a cyclohexyl group, a hydroxyhexamethylenyl group or $$-(CH_2-\underset{\underset{R'}{|}}{CH}-O)_nH$$

wherein R' represents a hydrogen atom and n is 2 or 3,
  $R^4$ is hydrogen atom or R—CH$_2$—CH= group wherein R represents an alkyl group of 1-8 carbon atoms,
  $R^5$ represents an alkyl group of 2-8 carbon atoms or a R—CH=CH— group wherein R represents an alkyl group of 1-8 carbon atoms, and
continuously removing the water formed during the process.

2. A process according to claim 1 wherein
  $R^1$ and $R^5$ are alkyl groups of 2-8 carbon atoms,
  $R^3$ is a linear or branched alkyl of 6 to 12 carbon atoms, and
  $R^4$ is hydrogen
and the molar ratio of aldehyde to alcohol is 0.5:1 to 10:1.

3. A process according to claim 1 wherein
  $R^1$ and $R^5$ are alkyl groups of 2-8 carbon atoms,
  $R^3$ is a cyclohexyl group, and
  $R^4$ is hydrogen
and the molar ratio of aldehyde to alcohol is 0.5:1 to 10:1.

4. A process according to claim 1 wherein
  $R^1$ is a R—CH$_2$—CH= group and $R^5$ is a R—CH=CH— group where R is an alkyl group of 1-8 carbon atoms,
  $R^3$ is an alkyl group of 6 to 12 carbon atoms, and
  $R^4$ is hydrogen
and the molar ratio of aldehyde to alcohol is 0.5:1 to 10:1.

5. A process according to claim 1 wherein
  $R^1$ is a R—CH$_2$CH= group and $R^5$ is a R—CH=CH— group where R is an alkyl group of 1-8 carbon atoms,
  $R^3$ is a cyclohexyl group, and
  $R^4$ is hydrogen
and the molar ratio of aldehyde to alcohol is 0.5:1 to 10:1.

6. A process according to claim 1 wherein
  $R^1$ and $R^5$ are alkyl groups of 2 to 8 carbon atoms,
  $R^4$ is hydrogen, and
  $R^3$ is a hydroxyhexamethylenyl group, and the molar ratio of aldehyde to alcohol is 0.05:1 to 10:1.

7. A process according to claim 1 wherein
  $R^1$ and $R^5$ are alkyl groups of 2 to 8 carbon atoms,
  $R^3$ is hydrogen, and
  $R^4$ is the group $$(CH_2-\underset{\underset{R'}{|}}{CH}-O)_nH$$

wherein R' is a hydrogen atom and the molar ratio of aldehyde t alcohol is 0.05:1 to 10:1.

8. A process according to claim 1 wherein
  $R^1$ is a R—CH$_2$—CH= group and $R^5$ is a R—CH=CH— group wherein R is an alkyl group having 1 to 8 carbon atoms,
  $R^4$ is hydrogen and
  $R^3$ is a hydroxyhexamethylenyl group,
and the molar ratio of aldehyde to alcohol is 0.05:1 and 10:1.

9. A process according to claim 1 wherein
  $R^1$ is a R—CH$_2$—CH= group and $R^5$ is a R—CH=CH— group wherein R is an alkyl group having 1 to 8 carbon atoms,
  $R^4$ is hydrogen, and
  $R^3$ is the group $$(CH_2-\underset{\underset{R'}{|}}{CH}-O)_nH$$

wherein R' is a hydrogen atom and the molar ratio of aldehyde to alcohol is 0.05:1 to 10:1.

* * * * *